(12) United States Patent
Saiki et al.

(10) Patent No.: US 10,821,201 B2
(45) Date of Patent: Nov. 3, 2020

(54) AIR PURIFIER

(71) Applicants: Mitsubishi Electric Corporation, Tokyo (JP); Mitsubishi Electric Home Appliance Co., Ltd., Saitama (JP)

(72) Inventors: Ayumi Saiki, Tokyo (JP); Sota Komae, Tokyo (JP); Akira Shiga, Tokyo (JP); Yosuke Kuge, Saitama (JP); Yoshitaka Akari, Saitama (JP); Kazuo Nyui, Saitama (JP)

(73) Assignees: Mitsubishi Electric Corporation, Tokyo (JP); Mitsubishi Electric Home Appliance Co., Ltd., Fukaya-shi (JP)

( * ) Notice: Subject to any disclaimer, the term of this patent is extended or adjusted under 35 U.S.C. 154(b) by 476 days.

(21) Appl. No.: 15/560,377

(22) PCT Filed: Mar. 30, 2015

(86) PCT No.: PCT/JP2015/059991
§ 371 (c)(1),
(2) Date: Sep. 21, 2017

(87) PCT Pub. No.: WO2016/157383
PCT Pub. Date: Oct. 6, 2016

(65) Prior Publication Data
US 2018/0064840 A1  Mar. 8, 2018

(51) Int. Cl.
*A61L 9/12* (2006.01)
*A61L 9/22* (2006.01)
*F24F 3/16* (2006.01)

(52) U.S. Cl.
CPC  *A61L 9/12* (2013.01); *A61L 9/22* (2013.01); *F24F 3/16* (2013.01);
(Continued)

(58) Field of Classification Search
CPC ................. A61L 9/12; A61L 9/22; F24F 3/16
See application file for complete search history.

(56) References Cited

U.S. PATENT DOCUMENTS

2005/0207951 A1* 9/2005 Lee .................. A61L 9/015
422/186.07
2008/0028936 A1* 2/2008 Takahashi .............. B01D 47/14
96/25
(Continued)

FOREIGN PATENT DOCUMENTS

CN  1665548 A  9/2005
EP  2730294 A1  5/2014
(Continued)

OTHER PUBLICATIONS

Office action dated Jun. 27, 2019 issued in corresponding CN patent application No. 201580077748.4 (and English translation thereof).
(Continued)

*Primary Examiner* — Sean E Conley
(74) *Attorney, Agent, or Firm* — Posz Law Group, PLC

(57) ABSTRACT

An air purifying operation is performed with a consideration for an influence of a purifying material on a person, and user's comfort and efficiency of the air purifying operation are both achieved. An air purifier includes a casing, an inlet, outlets, blowers, a decontamination unit, air ducts, movable louvers, a horizontal rotation mechanism, an ozone generation mechanism, human detection means, a control unit, or the like. The control unit detects whether or not there is a person in a room by the human detection means. Then, the control unit controls at least one of parameters including an ozone generation amount, a wind direction, an amount, and a speed of blown-out air based on the human detection result. Thus, if there is a person in the room, for example, a human avoiding operation, a human area operation, or the
(Continued)

like can be performed. If there is no person, an indoor air purifying operation for uniformly purifying air throughout the room can be performed.

15 Claims, 10 Drawing Sheets

(52) U.S. Cl.
CPC ...... *A61L 2209/111* (2013.01); *A61L 2209/14* (2013.01); *A61L 2209/212* (2013.01); *F24F 2003/1685* (2013.01); *F24F 2221/22* (2013.01)

(56) References Cited

U.S. PATENT DOCUMENTS

| | | | |
|---|---|---|---|
| 2008/0127830 A1* | 6/2008 | Le | B01D 53/0407 96/154 |
| 2009/0055102 A1 | 2/2009 | Laufer et al. | |
| 2010/0172793 A1* | 7/2010 | Obee | B01D 53/32 422/3 |
| 2011/0031322 A1* | 2/2011 | Zou | F24F 3/0442 236/1 B |
| 2011/0073686 A1 | 3/2011 | Uegaki et al. | |

FOREIGN PATENT DOCUMENTS

| | | |
|---|---|---|
| JP | H07-018582 B2 | 3/1989 |
| JP | H01-114633 A | 5/1989 |
| JP | 3582880 B2 | 10/2004 |
| JP | 2005-214432 A | 8/2005 |
| JP | 2006-314365 A | 11/2006 |
| JP | 2008-517276 A | 5/2008 |
| JP | 4533411 B2 | 9/2010 |
| JP | 2011-073617 A | 4/2011 |
| JP | 2011-196593 A | 10/2011 |
| JP | 2012-042160 A | 3/2012 |
| JP | 2012-097955 A | 5/2012 |
| TW | 201314140 A1 | 4/2013 |
| WO | 2011/045979 A1 | 4/2011 |

OTHER PUBLICATIONS

International Preliminary Report on Patentability dated Oct. 12, 2017 corresponding to PCT/JP2015/059991.
International Search Report of the International Searching Authority dated Jun. 30, 2015 for the corresponding international application No. PCT/JP2015/059991 (and English translation).
Office Action dated Oct. 21, 2016 issued in corresponding TW patent application No. 104119930 (and partial English translation).
Office Action dated Jan. 9, 2018 issued in corresponding JP patent application No. 2017-508902 (and English translation).

* cited by examiner

AIR PURIFIER

CROSS REFERENCE TO RELATED APPLICATION

This application is a U.S. national stage application of International Application No. PCT/JP2015/059991 filed on Mar. 30, 2015, the disclosure of which is incorporated herein by reference.

FIELD

The present invention relates to an air purifier having a function of purifying drawn-in air and blowing out the air.

BACKGROUND

As conventional technologies, for example, apparatuses as described in PTLs 1 to 3 are known. An air conditioner described in PTL 1 includes a deodorizing and disinfecting device provided in an air flow path. The deodorizing and disinfecting device includes an ozone generation device and a catalyst. An air purifier in PTL 2 includes a sterilization device that generates ions and a louver capable of closing an outlet. The air purifier alternately operates two blowers with the louver closing the outlet, thereby filling an inside of the air purifier with ions. An air purifier described in PTL 3 includes a shutter provided in an inlet, a reversely rotatable fan, and an ozonizer. For sterilization of an inside of the air purifier, the fan is reversely rotated with the shutter closing the suction port.

CITATION LIST

Patent Literature

[PTL 1] JP 1-114633 A
[PTL 2] Japanese Patent No. 4533411
[PTL 3] Japanese Patent No. 3582880

SUMMARY

Technical Problem

The conventional technologies in PTLs 1 to 3 described above have a configuration for deodorization, sterilization, or the like using a purifying material such as ozone or ions. However, for example, when the purifying material is used to purify the inside of the apparatus and then a blowing operation into a room is performed, consideration is needed for an influence of the purifying material remaining in air to be blown on a person in the room. Also, even when air containing the purifying material is to be blown into the room, consideration is needed for a person in the room. On the other hand, for example for the air purifier, too much consideration for the influence of the purifying material excessively limits a blowing operation into the room, a blowing area, or the like, which reduces efficiency of an air purifying operation. In this view, the conventional technologies do not consider a person in the room, and have a problem that it is difficult to perform the air purifying operation in a balanced manner with a consideration for a person.

The present invention is achieved to solve the above-described problem, and has an object to provide an air purifier capable of appropriately performing an air purifying operation with a consideration for an influence of a purifying material on a person, and achieving both users comfort and efficiency of the air purifying operation.

Solution to Problem

An air purifier according to the present invention includes: a casing having an inlet and an outlet of air; a blower for drawing air from the inlet into the casing and blowing the air out of the outlet; a decontamination unit configured to remove contaminants from the air drawn into the casing; an air duct configured to convey the air from which the contaminants are removed by the decontamination unit to the outlet; wind direction adjusting means capable of adjusting a wind direction of the air blown out of the outlet; purifying material generation means configured to generate a purifying material in the casing; human detection means configured to detect a physical quantity relating to a person; and control means having a function of actuating the wind direction adjusting means and the purifying material generation means, the control means configured to input an output of the human detection means to control at least one of parameters including a generation amount of the purifying material, a wind direction, an amount, and a speed of air blown out of the outlet.

Advantageous Effect of Invention

According to the present invention, at least one of parameters including a generation amount of a purifying material and a wind direction of blown-out air can be controlled based on a human detection result. This allows air purifying operation to be performed with a consideration for an influence of the purifying material on a person. This can achieve both user's comfort and efficiency of the air purifying operation.

DESCRIPTION OF EMBODIMENTS

Embodiment 1

Figure 1:
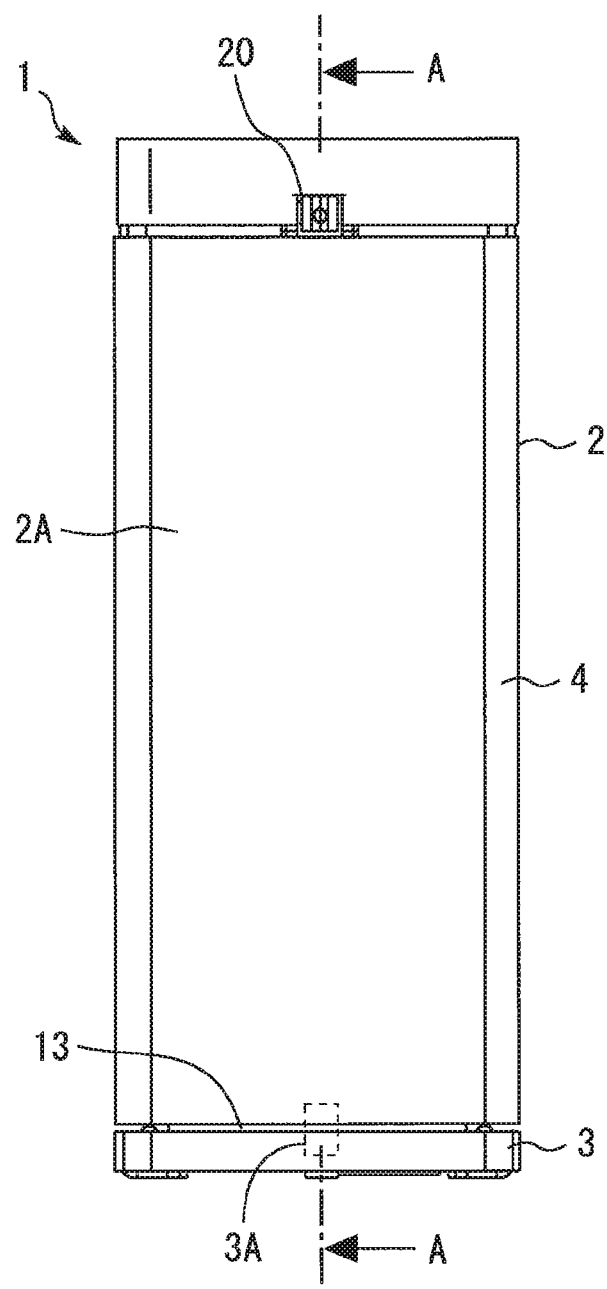
FIG. 1 is a front view of an air purifier according to Embodiment 1 of the present invention.

First, with reference to FIGS. 1 to 9, Embodiment 1 of the present invention will be described. In the drawings used herein, common elements are denoted by the same reference numerals, and overlapping descriptions are omitted. The present invention is not limited to the embodiments described below, but variations may be made without departing from the gist of the present invention. Also, the present invention covers all possible combinations of configurations and controls described in the embodiments below.

Figure 2:
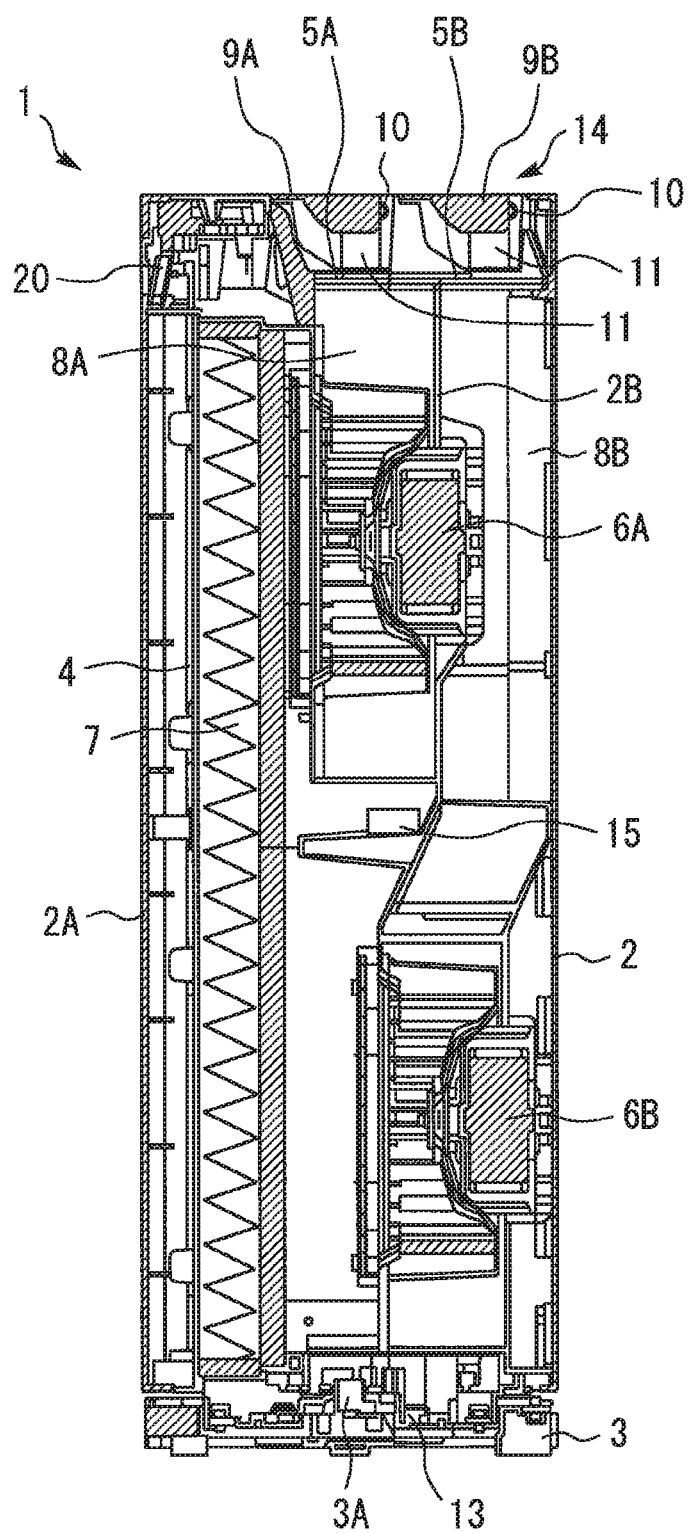
FIG. 2 is a sectional view of the air purifier taken at a position A-A denoted by an arrow in FIG. 1.

FIG. 1 is a front view of an air purifier according to Embodiment 1 of the present invention. FIG. 2 is a sectional view of the air purifier taken at a position A-A denoted by an arrow in FIG. 1. As shown in FIGS. 1 and 2, the air purifier 1 according to this embodiment includes a easing 2, a base 3, an inlet 4, outlets 5A, 5B, blowers 6A, 6B, a decontamination unit 7, air ducts 8A, 8B, movable louvers 9A, 9B, a louver drive 10, a rectification mechanism 11, a rectification drive 12, a horizontal rotation mechanism 13, an ozone generation mechanism 15, or the like. Among them, the inlet 4 and the outlets 5A, 5B open on the casing 2. The blowers 6A, 6B, the decontamination unit 7, the air ducts 8A, 8B, and the ozone generation mechanism 15 are housed in the casing 2.

The casing 2 is, for example, a substantially square cylindrical shape, and constituted by a vertically oriented tower-type case extending perpendicularly to a floor surface. To a front surface of the casing 2, a flat panel 2A covering the inlet 4 is removably mounted. The casing 2 is supported via a rotation axis 3A by the base 3 provided on the floor surface of a room. The easing 2 rotates horizontally on the base 3 around the rotation axis 3A. Basically herein, among side surfaces of the casing 2, a portion arranged to face a space in the room is referred to as a front surface, and a portion opposed to the front surface is referred to as a rear surface. In a horizontal direction, a direction of the front surface and the rear surface being opposed to each other is referred to as a front-rear direction, and a direction orthogonal to the front-rear direction is referred to as a lateral direction. The air purifier 1 is provided, for example, on the floor surface in a position near any wall in the room, and used with the rear surface of the casing 2 facing the wall surface and the front surface of the casing 2 facing the space in the room.

As shown in FIGS. 1 and 2, the inlet 4 is an opening for drawing air in the room into the casing 2, and has a vertically oriented opening shape extending vertically. The inlet 4 is placed, for example, in the front surface of the casing 2 and communicates with an outside via a gap formed between the easing 2 and the panel 2A. As shown in FIG. 2, the outlets 5A, 5B are two openings for blowing out air drawn into the casing 2 from the inlet 4. The outlets 5A, 5B are arranged in the front-rear direction in a top surface of the casing 2, and each extend laterally. Herein, the air blown out of the outlets 5A, 5B is sometimes referred to as "blown-out air". In the present invention, the inlet 4 may be placed in a back surface, the side surfaces, a bottom surface, or the like of the casing 2. The outlets 5A, 5B may be placed in the front surface, the side surface, or the like of the casing 2. Further, the number of the outlets is not limited to two, but in the present invention, only one or three or more outlets may be provided.

Figure 3:
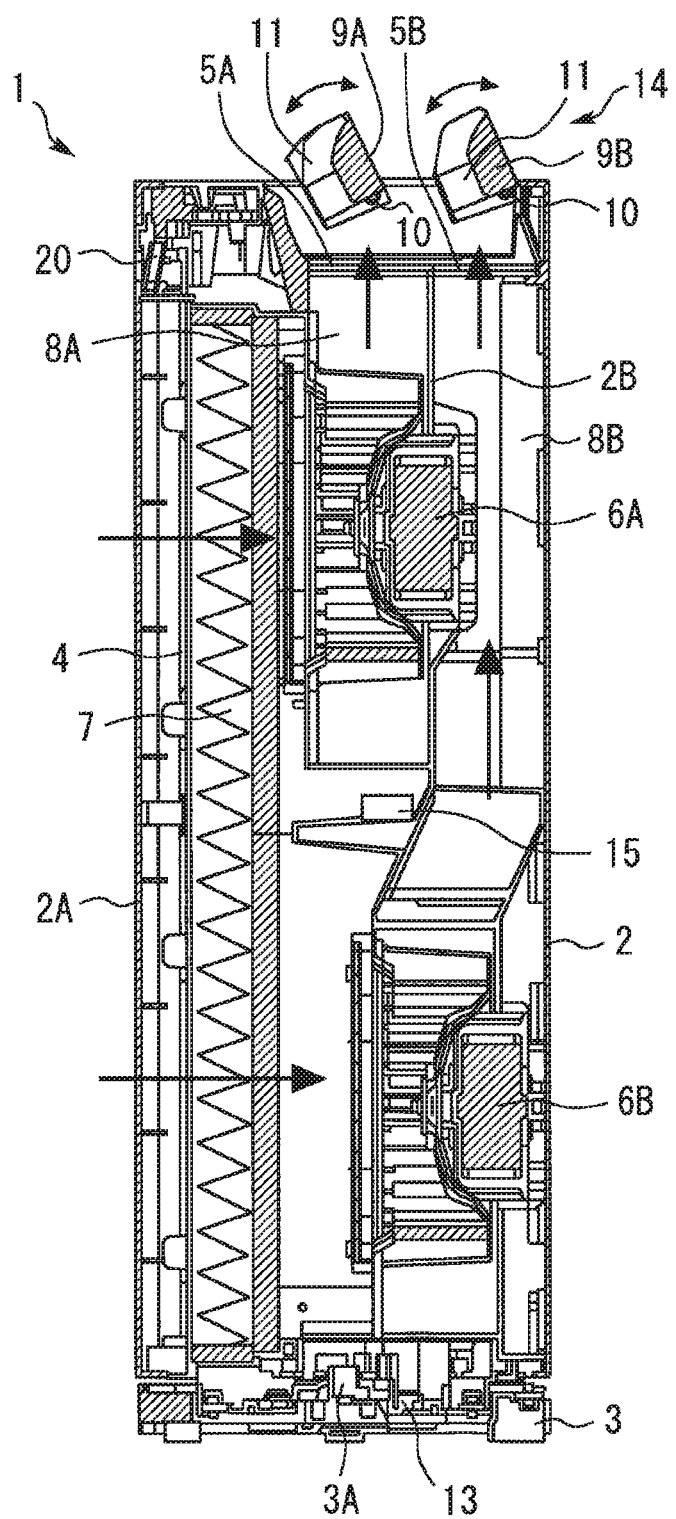
FIG. 3 is a sectional view similar to FIG. 2 showing a movable louver of the air purifier being swung upward.

As shown in FIG. 2, in a space from the inlet 4 to the outlets 5A, 5B within an internal space of the casing 2, the decontamination unit 7, the blowers 6A, 6B, and the air ducts 8A, 8B are arranged in order from an upstream side toward a downstream side. Thus, in the casing 2, as shown in FIG. 3 described later, a first air flow path extending from the inlet 4 through the decontamination unit 7, the blower 6A, and the air duct 8A to the outlet 5A, and a second air flow path extending from the inlet 4 through the decontamination unit 7, the blower 6B, and the air duct 8B to the outlet 5B are formed.

The blowers 6A, 6B draw air from the inlet 4 into the casing 2 and blow the air out of the outlets 5A, 5B. The blowers 6A, 6B each include, for example, a fan constituted by a centrifugal fan such as a sirocco fan, and an electric motor for rotating the fan. The blowers 6A, 6B are arranged to be shifted from each other in vertical and front-rear directions. The blower 6A located on an upper front side in the casing 2 is connected via the air duct 8A to the front outlet 5A. The blower 6B located on a lower rear side is connected via the air duct 8B to the rear outlet 5B. A rotation speed of the fan of the blower 6A is controlled by a control unit 30, and an amount of blown-out air changes according to the rotation speed of the fan.

The decontamination unit 7 purifies the air drawn into the casing 2. The decontamination unit 7 has a vertically oriented shape extending vertically, and is arranged between the inlet 4 and the two blowers 6A, 6B. The term "purification" means, for example, removing contaminants including dust, smoke, pollen, viruses, molds, bacteria, allergens, odor molecules, or the like suspended in the air. More specifically, "purification" means an operation for collecting, deactivating, disinfecting and adsorbing or decomposing the contaminants. The decontamination unit 7 includes, for example, a dust collection filter, a deodorization filter, an anti-mold and disinfection filter, a voltage application device, or the like, or a combination of these devices. The dust collection filter collects dust or the like, and the deodorization filter adsorbs odor components. The anti-mold and disinfection filter deactivates spores of mold or kills adhering bacteria. The voltage application device applies a high voltage across a pair of electrodes arranged in an air flow path to remove, deactivate, kill, destroy, or decompose the contaminants.

The air ducts 8A, 8B convey air purified by the decontamination unit 7 toward the outlets 5A, 5B. The air ducts 8A, 8B each vertically extend while being separated from each other by a partition 2B placed in the casing 2 and arranged in the front-rear direction. As such, in this embodiment, the two blowers 6A, 6B are arranged to be shifted in vertical and front-rear directions. The air ducts 8A, 8B arranged in the front-rear direction are connected to the blowers 6A, 6B. This configuration can facilitate formation of the air purifier 1 into a vertically oriented tower-type one and reduce a footprint thereof as compared to an air purifier that has a single blower to generate the same amount of air.

Figure 4:
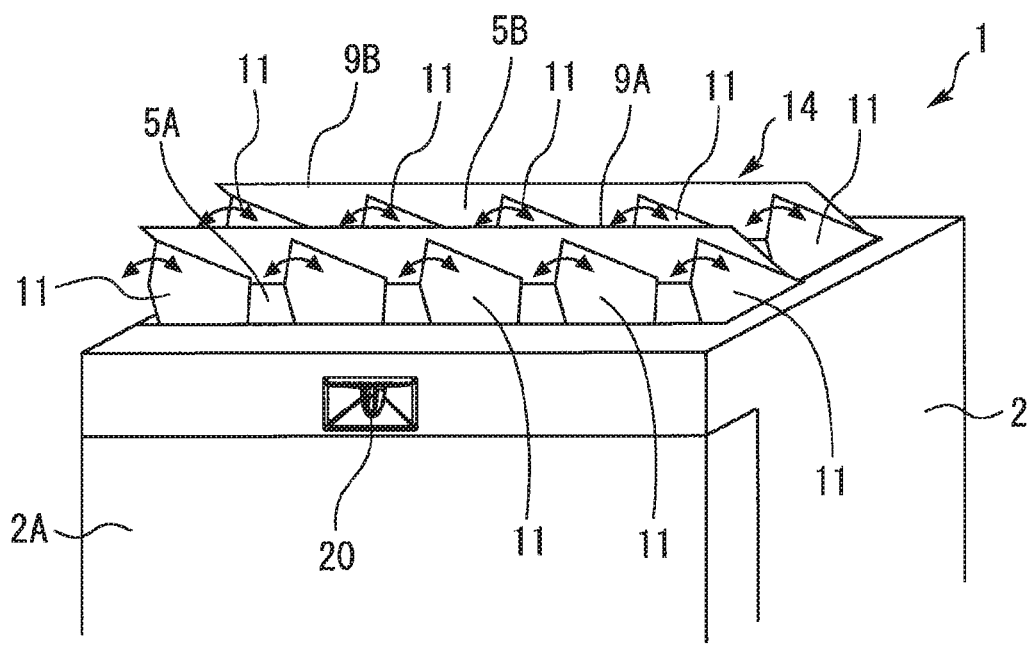
FIG. 4 is a perspective view of the movable louver and a rectification mechanism of the air purifier.

Next, with reference to FIGS. 3 and 4, the movable louvers 9A, 9B or the like of the air purifier 1 will be described. FIG. 3 is a sectional view similar to FIG. 2 showing the movable louver of the air purifier being swung upward. FIG. 4 is a perspective view of the movable louver and the rectification mechanism of the air purifier. FIG. 4 is a schematic diagram for describing a schematic structure, and does not necessarily match other drawings. As shown in FIGS. 3 and 4, the movable louvers 9A, 9B vertically adjust a wind direction (blowing direction) of the blown-out air, and are placed in the outlets 5A, 5B, respectively. The movable louvers 9A, 9B are formed of, fix example, elongated plates or the like extending laterally of the casing 2.

As shown in FIG. 3, a rear end of the front movable louver 9A is mounted via the louver drive 10 to a rear end of the outlet 5A. A rear end of the rear movable louver 9A is mounted via the other louver drive 10 to a rear end of the outlet 5B. The two louver drives 10 are mechanisms for vertically swinging the movable louvers 9A, 9B individually. Elevations of the blown-out air are vertically adjusted according to swing angles of the movable louvers 9A, 9B. The elevation angles of the blown-out air from the outlet 5A and the outlet 5B can be different from each other. The term "elevation angle" means an upward angle with reference to the horizontal direction. The movable louvers 9A, 9B may adjust a flow path area of the air blown out of the outlets 5A, 5B according to the swing angle. In particular, as shown in FIG. 2, the outlets 5A, 5B are closed by the movable louvers 9A, 9B with the movable louvers 9A, 9B being swung to a lowermost side.

The rectification mechanism 11 laterally adjusts the wind direction while keeping the elevation angle of the wind direction adjusted by the movable louvers 9A, 9B.

As shown in FIG. 4, the rectification mechanism 11 includes a plurality of fins standing on wind receiving surfaces of the movable louvers 9A, 9B. The fins are laterally arranged with clearances therebetween. The rectification mechanism 11 is laterally swung by the rectification drive 12 (see FIG. 5) to laterally change the wind direction of the blown-out air according to the swing angle. An angle of the blown-out air with respect to the horizontal direction (hereinafter referred to as a rotation angle) is mainly adjusted by the horizontal rotation mechanism 13. On the other hand, the rectification mechanism 11 can laterally fine-adjust the wind direction of the blown-out air, and increase directivity of the blown-out air with respect to a target wind direction.

As shown in FIGS. 1 to 3, the horizontal rotation mechanism 13 is provided between the casing 2 and the base 3. The horizontal rotation mechanism 13 horizontally rotates the casing 2 around the rotation axis 3A. Thus, the wind direction of the blown-out air is horizontally (that is, laterally) adjusted by the horizontal rotation mechanism 13. The movable louvers 9A, 9B, the rectification mechanism 11, and the horizontal rotation mechanism 13 constitute wind direction adjusting means 14 in this embodiment. This configuration allows the wind direction of the blown-out air to be set separately in the vertical and lateral directions, and allows the air to be accurately blown to a desired position in a three-dimensional space. Further, the horizontal blowing direction is variable, thereby allowing the air to be blown to every corner in the room. This allows contaminants in the room to be drawn into the casing 2, and allows more contaminants to be treated by the decontamination unit 7. Also, it is known that among the contaminants, molds, bacteria, and some allergens grow, and accumulation thereof reduces sanitation in the casing 2. This requires means for improving sanitation in the casing 2. In this respect, in this embodiment, the horizontal rotation mechanism 13 allows the air to be blown to every corner in the room, thereby improving sanitation in the room. The purifying material generation means 15 can improve sanitation in the casing 2, thereby improving overall sanitation in a human living space.

The ozone generation mechanism 15 generates in the casing 2 at least ozone among purifying materials for purifying air such as ozone, various radicals, or ions. As shown in FIG. 2, the ozone generation mechanism 15 is provided, for example, in a space communicating with a suction side of the blowers 6A, 6B in an internal space of the casing 2. Also, the ozone generation mechanism 15 includes, for example, a pair of electrodes (not shown) facing each other. A high voltage is applied across the electrodes to generate active oxygen such as ozone. In the ozone generation mechanism 15, the control unit 30 described later can change the voltage applied across the electrodes to control an ozone generation amount. In this embodiment, the ozone generation mechanism 15 is a specific example of the purifying material generation means, and the ozone is an example of the purifying material for purifying air.

Figure 5:
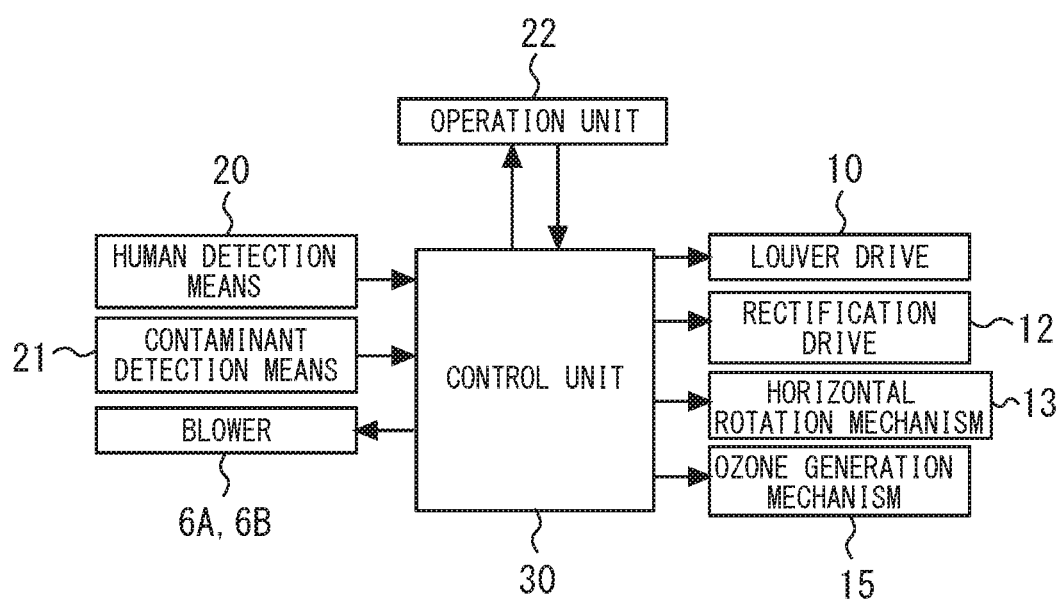
FIG. 5 is a configuration diagram of a control system of the air purifier according to Embodiment 1 of the present invention.

Next, with reference to FIG. 5, a control system of the air purifier 1 will be described. FIG. 5 is a configuration diagram of the control system of the air purifier according to Embodiment 1 of the present invention. As shown in FIG. 5, the air purifier 1 includes a sensor system including human detection means 20 and contaminant detection means 21, an operation unit 22 operated by a user, and the control unit 30 that controls an operation state of the air purifier 1. The human detection means 20 detects whether or not there is a person in the room provided with the air purifier 1. More specifically, the human detection means 20 detects a physical quantity relating to a person (that is, a physical quantity reflected by presence or absence of a person). As shown in FIGS. 1 and 4, the human detection means 20 includes, for example, an infrared sensor, an image recognition sensor, a pyroelectric sensor, or the like, and is placed in a front upper portion of the casing 2. In the present invention, the human detection means 20 may include other sensors capable of detecting a person. The human detection means 20 may include a movable sensor that has detection unit capable of being swung laterally. In this case, the detection unit can be swung to search the inside of the room without rotating the casing.

The contaminant detection means 21 detects an amount of contaminants in the air drawn in from the inlet 4, and includes, for example, a dust sensor, a gas sensor, an odor sensor, or the like. The contaminant detection means 21 is placed, for example, in an upstream side of the decontamination unit 7 in an air flow direction in the casing 2. The dust sensor includes a semiconductor device, an optical device, or the like, and detects a concentration of dust, smoke, pollen, or the like in the air. The gas sensor detects a concentration of a specific gas component corresponding to contaminants. The odor sensor includes a semiconductor device, a piezoelectric element, or the like, and detects concentrations of several types of gas components that cause odor (odor gases)

The control unit 30 includes a microcomputer or the like, and includes a memory circuit that stores a defined control program, a processor (CPU) for executing the control program, and an input/output port that inputs and outputs signals to the processor. As shown in FIG. 5, the sensor system including the human detection means 20 and the contaminant detection means 21 are connected to an input side of the control unit 30. Actuators such as the blowers 6A, 6B, the louver drive 10, the rectification drive 12, the horizontal rotation mechanism 13, the ozone generation mechanism 15, or the like are connected to an output side of the control unit 30. The control unit 30 is connected to the operation unit 22 so as to be able to communicate with each other. The control unit 30 actuates the actuators based on set contents of the operation unit 22 operated by the user, an output of the sensor system, or the like to control the air purifier 1.

(Basic Air Purifying Operation)

Next, a basic operation of the air purifier 1 will be described. When operating the air purifier 1, the control unit 30 drives the blowers 6A, 6B. Thus, as shown by an arrow in FIG. 3, the air in the room is drawn in from the inlet 4 into the casing 2, and the air passes through the decontamination unit 7 and is thus purified. Then, a part of the purified air passes through the upper blower 6A and the air duct 7A 8A to the outlet 5A, and is blown out of the outlet 5A.

Remaining purified air passes through the lower blower 6B and the air duct 7B 8B to the outlet 5B, and is blown out of the outlet 5B. As such, the air purified by the air purifier 1 is blown out of the outlets 5A, 5B into the room. The blown-out air circulates in the room, and is then drawn in together with contaminants in the air into the inlet 4. This circulation operation is repeated to purify the air in the room.

At this time, the control unit 30 drives the louver drive 10, the rectification drive 12, and the horizontal rotation mechanism 13 based on set contents of the operation by the user, a detection result of the sensor system, or the like to control the state of the blown-out air. Specifically, the elevation angle of the wind direction of the blown-out air is adjusted according to the swing angle of the movable louvers 9A, 9B. The rotation angle of the wind direction is adjusted by the rectification mechanism 11 and the horizontal rotation mechanism 13. Changing the swing angle of the movable louvers 9A, 9B changes a flow path area of the blown-out air, thereby adjusting a speed of the blown-out air. Further, an amount of the blown-out air is adjusted according to a rotation speed of the blowers 6A, 6B. The control unit 30 changes the elevation angle, the rotation angle, the amount and the speed as required while continuing the circulating operation described above to purify the air throughout the room.

Next, operation modes of the air purifier 1 will be described. The control unit 30 has a function of performing an inside cleaning operation, a human avoiding operation, a human area operation, and an indoor air purifying operation. These four types of operations correspond to first to fourth operation modes.

(Inside Cleaning Operation)

The inside cleaning operation is an operation mode (first operation mode) in which ozone is used to purify the space in the casing. In the inside cleaning operation, first, as shown in FIG. 2, the movable louvers 9A, 9B close the outlets 5A, 5B. Then, with the blowers 6A, 6B being stopped, the ozone generation mechanism 15 is actuated. This allows the casing 2 to be filled with ozone generated by the ozone generation mechanism 15 to purify the inside of the casing 2. This allows the inside of the air purifier 1 to be deodorized and sterilized.

After the inside cleaning operation is performed, ozone having a relatively high concentration may remain in the casing 2. If the air purifying operation is performed as in normal time in this state, air containing the remaining ozone may be blown toward a person in the room, thereby having an influence such as discomfort on the person. Thus, in the case where the inside cleaning operation is performed and then the air purifying operation in the room is performed, the control unit 30 controls at least one of parameters including the ozone generation amount in the casing 2 and the wind direction of the blow-out air based on a human detection result by the human detection means 20 and an ozone amount index.

The term "ozone amount index" means various indices having a correlation to the amount of the ozone generated by the ozone generation mechanism 15. A specific example of the ozone amount index includes, for example, an ozone concentration detected by an ozone concentration sensor or the like, a voltage applied across the electrodes of the ozone generation mechanism 15, an actuation time of the ozone generation mechanism 15, an elapsed time since the ozone generation mechanism 15 stops, or the like. The ozone concentration sensor is provided in the casing 2 as required, and can directly detect the ozone concentration.

The ozone concentration in the casing 2 increases as the voltage applied across the electrodes of the ozone generation mechanism 15 increases. The ozone concentration increases as the actuation time of the ozone generation mechanism 15 increases, and decreases as the elapsed time since the ozone generation mechanism 15 stops increases. Thus, the voltage and the times can be used as the ozone amount indices. In other words, the control unit 30 can change at least one of the voltage, the actuation time, and the elapsed time to control the ozone concentration, that is, the ozone generation amount in the casing 2.

The air purifier 1 may perform an operation for blowing air containing ozone into the room at timing irrelevant to the inside cleaning operation (hereinafter referred to as a special air purifying operation). In the special air purifying operation, the air purifying operation described above is performed while the ozone generation mechanism 15 is being actuated. Also in this case, the control unit 30 controls at least one of the parameters including the ozone generation amount in the casing 2 and the wind direction of the blown-out air based on the human detection result by the human detection means 20 and the ozone amount index. An operation mode switching control described below is such that any of the human avoiding operation, the human area operation, and the indoor air purifying operation is select based on the human detection result and the ozone amount index to switch the control of the wind direction. The operation mode switching control can be applied both after the inside cleaning operation and during the special air purifying operation.

(Human Avoiding Operation)

The human avoiding operation is an operation mode (second operation mode) performed in the case where the air purifying operation is performed with a person in the room being detected and the ozone amount index being higher than an upper limit reference value. In the human avoiding operation, the wind direction adjusting means 14 is actuated with reference to a direction of the person detected to set the wind direction of the blown-out air to a direction without a person. Specifically, in the human avoiding operation, for example, the horizontal rotation mechanism 13 may be controlled to blow air so as to avoid a direction with a person in the horizontal direction. In the direction with a person, the movable louvers 9A, 9B may be controlled to change the wind direction upward to blow air so as to avoid a person.

More specifically, in the human avoiding operation, it is preferable that the wind direction of the blown-out air is swung in the horizontal direction throughout the room, while the wind direction is changed upward to avoid a person in the direction with the person. Thus is the air throughout the room can be purified efficiently while avoiding blowing air toward a person. The human avoiding operation in the present invention also includes an operation for fixing the wind direction of the blown-out air to a particular direction without a person.

The "upper limit reference value" is set, for example, correspondingly to a maximum value of an ozone concentration that is allowed to be blown out together with air toward a person, and is stored in advance in the control unit 30. Specifically, for using a detected ozone concentration as the ozone amount index, a maximum allowable value of the ozone concentration may be set as the upper limit reference value. For using the actuation time of the ozone generation mechanism 15 as the ozone amount index, an actuation time when the ozone concentration in the casing 2 reaches the maximum allowable value may be set as the upper limit reference value.

By the human avoiding control, even if the ozone of a high concentration remains in the casing 2 due to the inside cleaning operation, the air purifying operation can be quickly started by blowing air in the direction without a person. Thus, for example, even if the operation for purifying the air is performed immediately after the inside cleaning operation, there is no need to wait until the ozone concentration decreases. This can improve user's convenience. Also, the human avoiding control can prevent the air containing the ozone of a high concentration from being blown toward a person to have an influence such as discomfort on the person both after the inside cleaning operation and during the special air purifying operation.

(Human Area Operation)

The human area operation is an operation mode (third operation mode) performed in the case where the air purifying operation is performed with a person in the room being detected and the ozone amount index being equal to or lower than the upper limit reference value. In the human area operation, the wind direction adjusting means 14 is actuated with reference to a direction of the person detected to set the wind direction of the blown-out air to a direction with a person.

Thus, the air purifier 1 preferentially purifies air in an area with a person in the room. In the human area operation, it is preferable that once it is determined that the area with a person has been purified, the wind direction of the blown-out air is changed to another area (direction) to sequentially purify each area throughout the room. However, in the human area operation of the present invention, the wind direction of the blown-out air may be fixed to a particular direction with a person.

By the human area operation, when the blown-out air has a property such that the air is allowed to be blown toward a person, air around the person can be preferentially purified. Thus, for example, in a short time after the activation of the air purifier 1, comfort by air purification can be provided to the user. This allows the air purifying operation with high user's convenience. Also, in the case of using a purifying material that is more preferably released toward the user, if in an appropriate amount, such as negative ions, the human area operation can cause the appropriate amount of purifying material to efficiently reach around the user. Thus, comfort by the purifying material can be provided to the user effectively.

(Indoor Air Purifying Operation)

The indoor air purifying operation is an operation mode (fourth operation mode) performed in the case where the air purifying operation is performed without a person being detected. In the indoor air purifying operation, the wind direction adjusting means 14 is actuated to blow air while distributing the blown-out air throughout the room. Thus, the air purifier 1 can efficiently uniformly purify the air throughout the room. This can ensure a comfort environment when the user enters the room.

(Human Corresponding Generation Amount Control)

In the operation mode switching control described above, the case where the operation mode is selected (that is, the wind direction of the blown-out air is switched) based on the human detection result and the ozone amount index has been described. In addition to this, in this embodiment, human corresponding generation amount control may be performed for controlling the ozone generation amount based on the human detection result and the ozone amount index. In the human corresponding generation amount control, the e generation amount is reduced to a human allowable reference value or lower, for example, when a person is detected in the room. When no person is detected in the room, the ozone generation amount is set to a normal reference value higher than the human allowable reference value.

The "human allowable reference value" is set, for example, correspondingly to a maximum value of the concentration of ozone that is allowed to be blown into the room with a person. The "normal reference value" is set, for example, correspondingly to an ozone concentration that provides a maximum effect of ozone for air purification or the like irrespective of presence of a person. The human allowable reference value and the normal reference value are stored in advance in the control unit 30. Also, the control of the ozone generation amount is achieved by directly controlling the ozone concentration or controlling the actuation time of the ozone generation mechanism 15 as described above.

By the human corresponding generation amount control, when there is a person in the room, the ozone concentration in the blown-out air can be reduced to reduce the influence of ozone on the person to an allowable level. This can improve user' convenience while keeping an air purifying effect by the ozone. In the present invention, the operation mode switching control described above and the human corresponding generation amount control may be combined. The human corresponding generation amount control may be used solely without the operation mode switching control. The human allowable reference value may be set to the same as or different from the upper limit reference value described above.

(Contamination Corresponding Control)

In this embodiment, contamination corresponding control for controlling the ozone generation amount based on the detection result of the contaminant detection means 21 may be performed. Specifically, in the contamination corresponding control, when the contaminant concentration detected by the contaminant detection means 21 is a contamination determination value or higher, the ozone generation amount is increased as compared to a case where the contaminant concentration is lower than the contamination determination value. The "contamination determination value" is set, for example, correspondingly to a relatively high concentration of contaminants that appears to be preferably purified with ozone, and is stored in advance in the control unit 30. In the contamination corresponding control, instead of a process of increasing the ozone generation amount, an output of the blowers 6A, 6B (the amount of blown-out air) may be increased. Further, both the ozone generation amount and the amount of blown-out air may be increased.

By the contamination corresponding control, when the air contains a large amount of contaminants, an amount of ozone released into the room can be increased to efficiently purify the contaminants. Also, the amount of blown-out air is increased to increase an amount of air circulated in the room, thereby increasing efficiently of purification. This allows quick purification of the contaminants in the room.

Specific Processes for Realizing Embodiment 1

Figure 6:
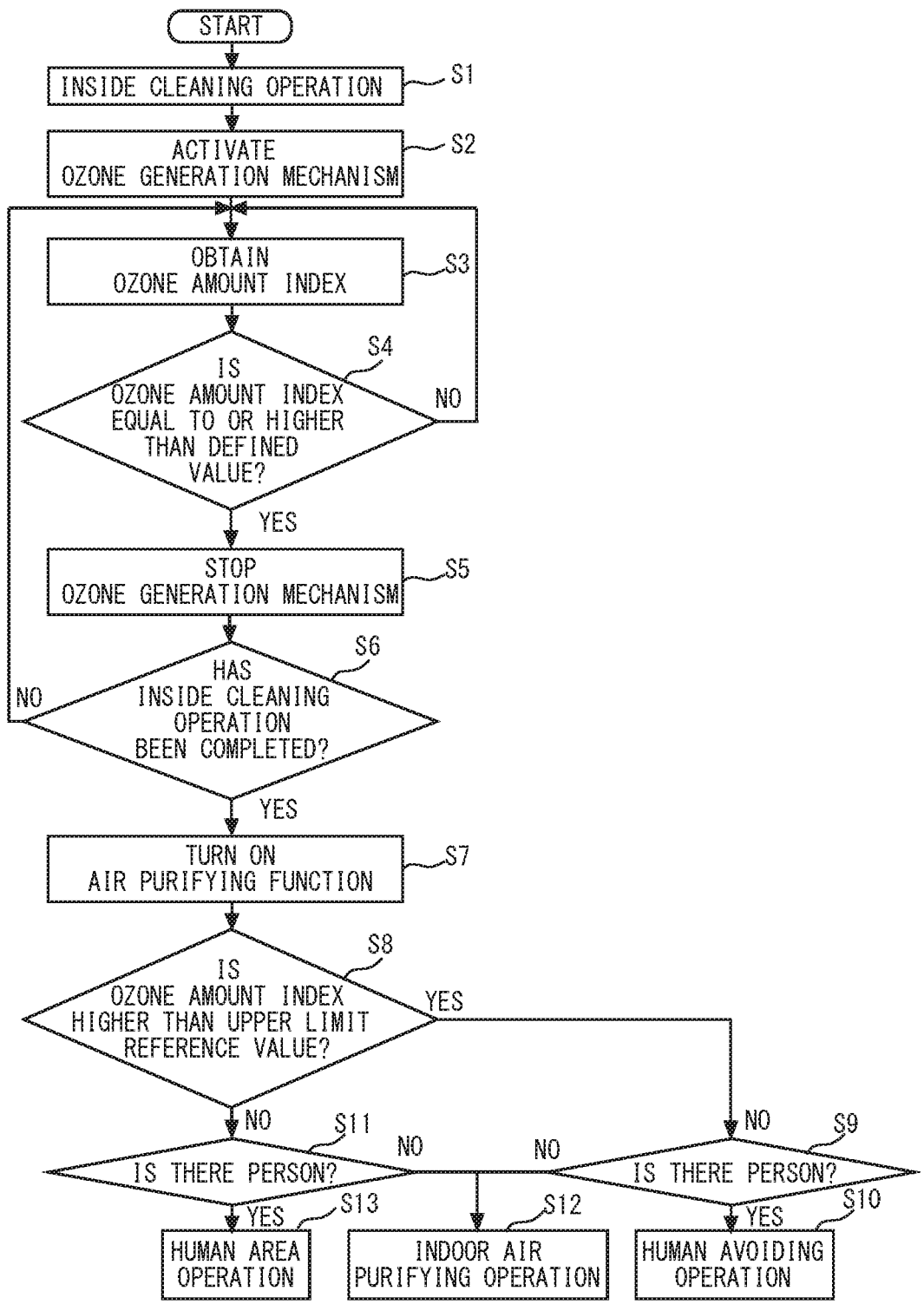
FIG. 6 is a flowchart showing an example of controls of the air purifier in Embodiment 1 of the present invention.
Figure 7:
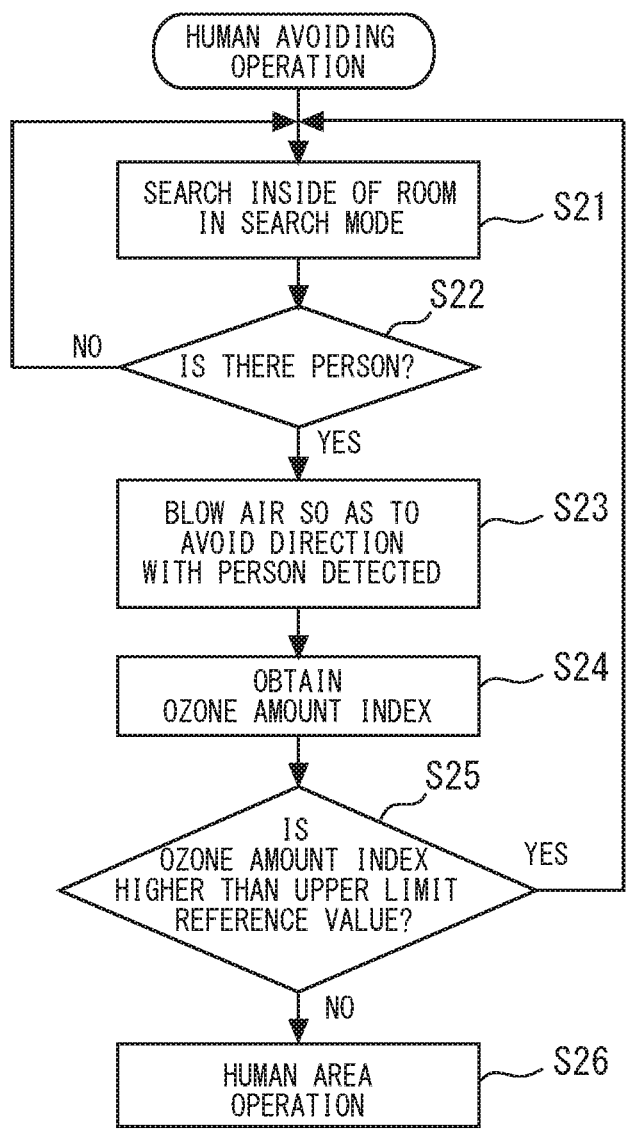
FIG. 7 is a flowchart showing a human avoiding operation in FIG. 6.
Figure 8:
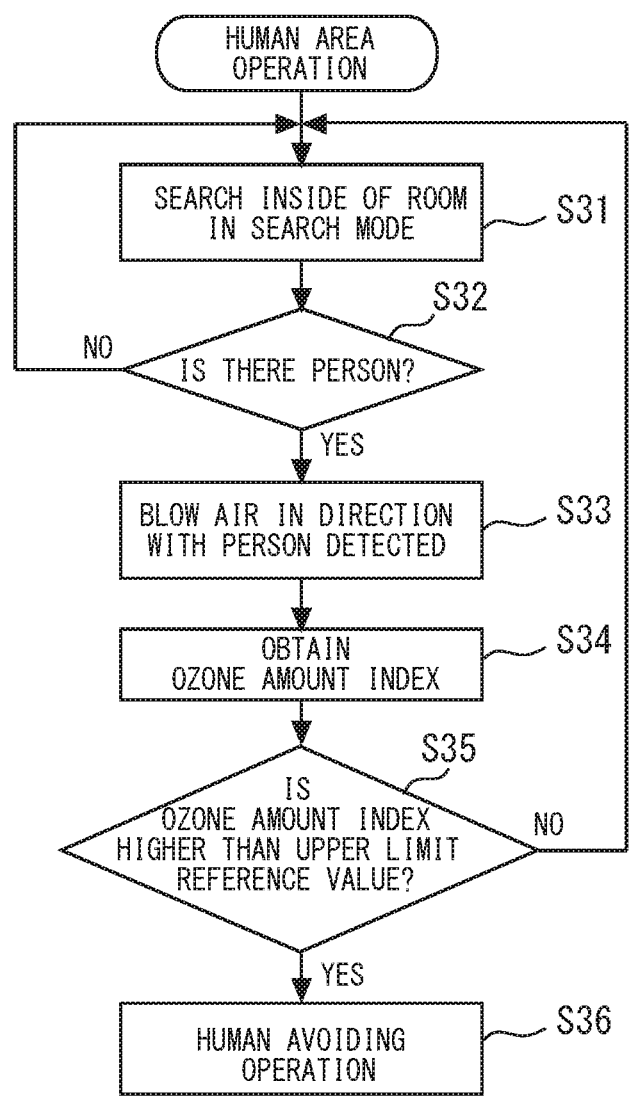
FIG. 8 is a flowchart showing a human area operation in FIG. 6.

Next, with reference to FIGS. 6 to 8, specific processes for realizing the control described above will be described. First, FIG. 6 is a flowchart showing an example of the control of the air purifier in Embodiment 1 of the present invention. In a routine shown in FIG. 6, in step S1, the inside cleaning operation is performed, for example, when at least one of inside cleaning conditions (1) to (3) described below is satisfied.

(1) A case where the user performs an operation to start the inside cleaning operation.

(2) A case where a cumulative actuation time as a total value of times when the air purifying operation was performed in the past reaches a reference time when the inside cleaning operation is to be performed.

(3) A case where the concentration of an odor gas in the casing 2 detected by the odor sensor or the like exceeds an allowable upper limit value.

Next, in step S2, the ozone generation mechanism 15 is activated to generate ozone in the casing 2. In step S3, an ozone amount index corresponding to the ozone concentration in the casing is obtained by the method described above. Then, in step S4, it is determined whether the ozone amount index is equal to or higher than a defined value set in advance or not. The defined value is set, for example, correspondingly to the ozone concentration required for deodorization, sterilization, or the like. If the determination in step S3 is not satisfied, ozone does not accumulate in the casing 2 to a sufficient concentration, and thus the processes in steps S3, S4 are repeated while the ozone generation mechanism 15 is being actuated. If the determination in step S4 is satisfied, the process moves to step S5 to stop the ozone generation mechanism 15.

Next, in step S6, it is determined whether or not the inside cleaning operation has been completed. In this determination process, for example, it is determined whether or not a duration of the inside cleaning operation has reached a defined purification completion time. The duration may be, for example, an elapsed time since the ozone generation mechanism 15 is activated. Also, the duration may be an elapsed time since step S4 is satisfied, or an elapsed time since a detection value of the odor sensor decreases to a defined purification completion concentration or lower. Further, in step S6, it may be determined, for example, whether or not the ozone concentration is the purification completion concentration or higher, or whether or not the odor gas concentration is an allowable odor concentration or lower.

If the determination in step S6 is satisfied, the process moves to step S7, and an air purifying function is turned on. Specifically, in step S7, the blowers 6A, 6B are activated, and the movable louvers 9A, 9B are swung upward to open the outlets 5A, 5B, thereby moving to a state allowing the air purifying operation. On the other hand, if the determination in step S6 is not satisfied, the process returns to step S3 to continue the inside cleaning operation.

Next, in step S8, it is determined whether or not the ozone amount index is higher than the upper limit reference value. If the determination in step S8 is satisfied, the process moves to step S9, and it is determined whether or not there is a person in the room based on the human detection result by the human detection means 20. Then, if the determination in step S9 is satisfied, the process moves to step S10 to perform the human avoiding operation. If the determination in step S9 is not satisfied, there is no person in the room, and thus the process moves to step S12 to perform the indoor air purifying operation. On the other hand, if the determination in step S8 is not satisfied, in step S11, it is determined whether or not there is a person in the room. Then, if the determination in step S11 is satisfied, the process moves to step S13 to perform the human area operation. If the determination in step S11 is not satisfied, in step S12, the indoor air purifying operation is performed.

Next, with reference to FIG. 7, a specific example of the human avoiding operation will be described. FIG. 7 is a flowchart showing the human avoiding operation in FIG. 6. In the routine in FIG. 7, first in steps S21, S22, it is determined whether or not there is a person in the room for each direction while performing a search mode. The search mode is such that the horizontal rotation mechanism 13 is actuated to rotate a human detection direction by the human detection means 20 together with the casing 2 in the horizontal direction to scan each direction in the room. Then, if the determination in step S22 is satisfied by a person being detected in any direction, the process moves to step S23. In step S23, air is blown so as to avoid a direction with a person detected to perform the air purifying operation so as not to direct the blown-out air toward the person.

On the other hand, the determination in step S22 is not satisfied, the processes in steps S21, S22 are repeated to continue the search mode until a person enters the room. In this case, it may be determined that there is no person in the room, and the process may move to the indoor air purifying operation. Thus, for example, if a person exits from the room, the process can move to an operation mode in the absence of a person to efficiently purify the air throughout the room.

Next in step S24, the ozone amount index is obtained similarly to the above, and in step S25, it is determined whether or not the ozone amount index is higher than the upper limit reference value. Then, if the determination in step S25 is not satisfied, it is determined that the ozone concentration in the blown-out air has decreased to a level that has no influence on a person, and thus the process moves to the human area operation in step S26. If the determination in step S25 is satisfied, the process returns to step S21 to continue the human avoiding operation.

Next, with reference to FIG. 8, a specific example of the human area operation will be described. FIG. 8 is a flowchart showing the human area operation in FIG. 6. In the routine in FIG. 8, first in steps S31, S32, it is determined whether or not there is a person in the room for each direction while performing the search mode described above. Then, if the determination in step 32 is satisfied by a person being detected in any direction, the process moves to step 33. In step S33, air is blown in a direction with a person detected to perform the air purifying operation in that direction. On the other hand, if the determination in step 32 is not satisfied, the processes in steps S31, S32 are repeated to continue the search mode until a person enters the room. In this case, it may be determined that there is no person in the room, and the process may move to the indoor air purifying operation.

Next in step S34, an ozone amount index is obtained similarly to the above, and in step S35, it is determined whether or not the ozone amount index is higher than the upper limit reference value. Then, if the determination in step S35 is satisfied, it is determined that the ozone concentration in the blown-out air has increased to a level that has an influence on a person, and thus the process moves to the human avoiding operation in step S36. If the determination in step S35 is not satisfied, the process returns to step S31 to continue the human area operation. An example of the determination in step S35 being satisfied includes, for example, a case where the ozone concentration in the blown-out air has increased when air is blown while generating the ozone by the special air purifying operation.

Figure 9:
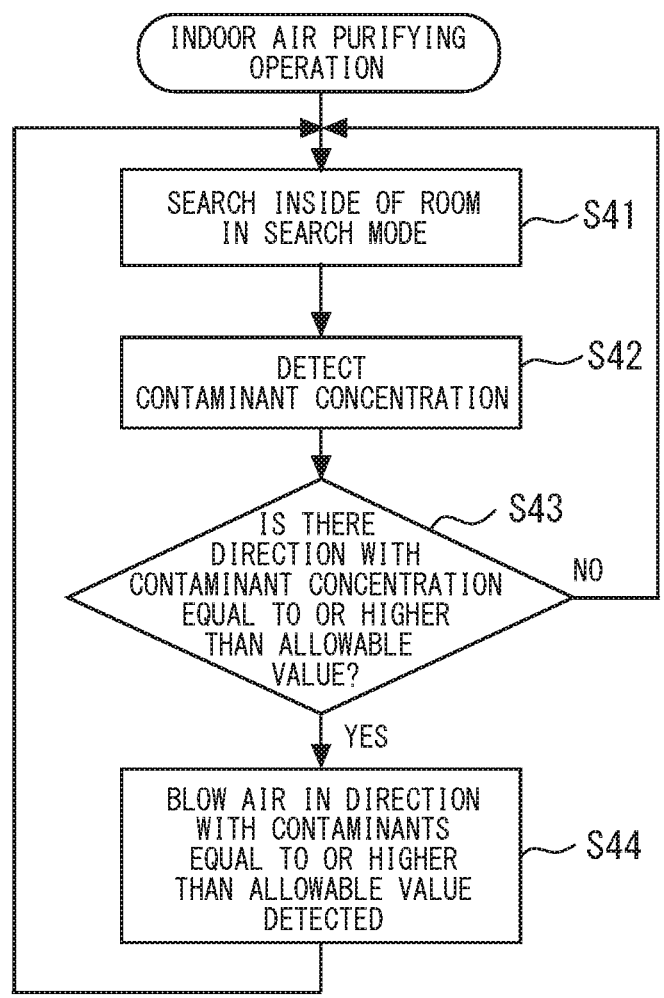
FIG. 9 is a flowchart showing a human indoor air purifying operation in FIG. 6.

Next, with reference to FIG. 9, a specific example of the indoor air purifying operation will be described. FIG. 9 is a flowchart showing the human area operation in FIG. 6. In the routine in FIG. 9, first in steps S41, S42, a contaminant concentration in the air is detected by the contaminant detection means 21 while performing a search mode. The search mode of the indoor air purifying operation is such that a contaminant concentration in the air flowing back to a position of the air purifier 1 is detected for each direction while the horizontal rotation mechanism 13 is rotating an air blow-out direction.

Next in step S43, based on a result of the search mode, it is determined whether or not there is a direction with a contaminant concentration equal to or higher than a defined allowable value. Then, if the determination in step S43 is satisfied, the process moves to step S44, and the blown-out air is blown in the direction with contaminants equal to or higher than the allowable value detected. If the determination in step S43 is not satisfied, the process returns to step S41 to continue the indoor air purifying operation.

As described above in detail, according to this embodiment, the wind direction of the blown-out air and the ozone concentration in the casing 2 may be controlled based on the human detection result and the ozone amount index. Thus, for example, in the case where the air purifying operation is performed after the inside cleaning operation, the human avoiding operation, the human area operation, and the indoor air purifying operation can be appropriately used based on the presence or absence of a person and the level of the ozone concentration. Similarly, also in the special air purifying operation for blowing the blown-out air containing ozone, the operations described above can be appropriately used. This allows purification in the casing 2 and the air purifying operation using the ozone with a consideration for the influence of the ozone on a person. This can achieve both user's comfort and efficiency of the air purifying operation.

According to this embodiment, if at least one of the human detection result and the ozone amount index changes while the human avoiding operation and the human area operation are being performed, the operation mode is switched according to a state of after the change. Thus, even if a person often enters and exits from the room and the ozone concentration often increases and decreases, an appropriate operation mode can be always selected. Thus, an air purifying effect can be produced to the maximum without having an influence on a person.

Also, in an example of this embodiment, the actuation time of the ozone generation mechanism 15 and the elapsed time since the ozone generation mechanism 15 stops are used as the ozone amount indices. This allows the ozone generation amount to be indirectly detected even without an ozone concentration sensor. This can simplify a structure of the air purifier 1, and promote a reduction in cost. The air purifier 1 includes the two outlets 5A, 5B, blowers 6A, 6B, and movable louvers 9A, 9B. Thus, the air can be blown from the outlets 5A, 5B in two directions, thereby allowing the blown-out air to be appropriately distributed as required. As an example, in the human area operation, the air can be blown from the front outlet 5A toward a person, while the air can be blown from the rear outlet 5B in a direction that allows an increase in purification efficiency throughout the room.

Embodiment 2

Figure 10:
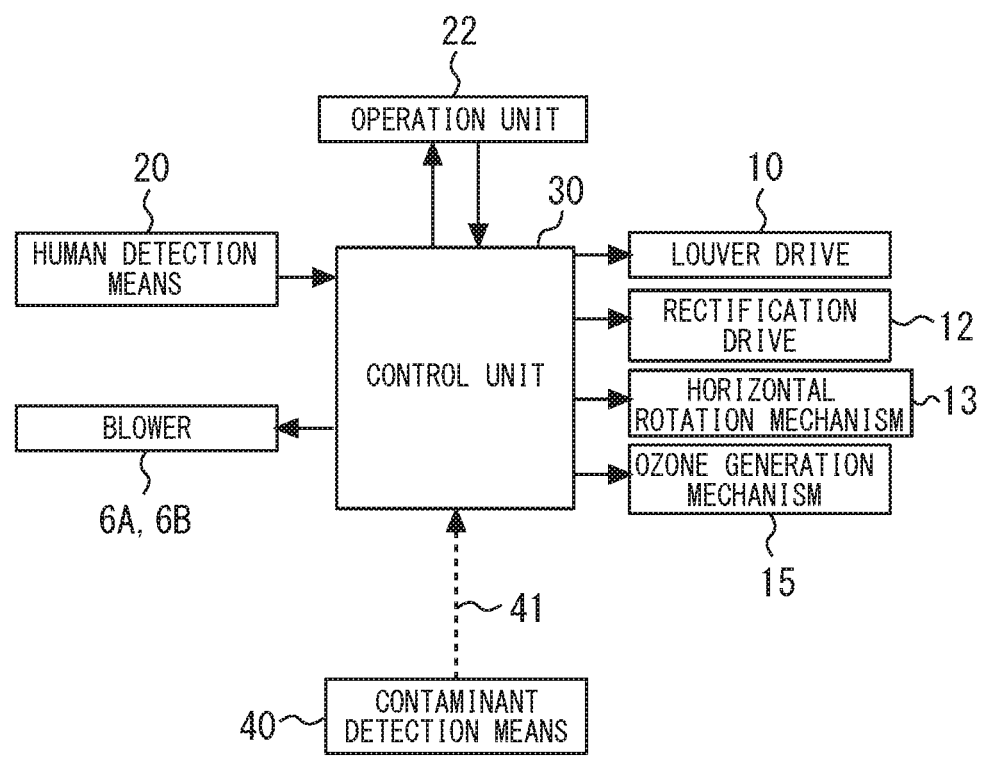
FIG. 10 is a configuration diagram of a control system for an air purifier according to Embodiment 2 of the present invention.

Next, with reference to FIG. 10, Embodiment 2 of the present invention will be described. This embodiment is characterized by using movable contaminant detection means. FIG. 10 is a configuration diagram of a control system for an air purifier according to Embodiment 2 of the present invention. As shown in FIG. 10, the air purifier 1 of this embodiment includes movable contaminant detection means 40. The contaminant detection means 40 has a function similar to that of the contaminant detection means 21 in Embodiment 1 above, and is formed as a component separate from the casing 2. The contaminant detection means 40 is set up away from the casing 2 and configured to transmit a detection result of contaminants via wired or wireless remote communication means 41 to the control unit 30.

This embodiment thus configured can provide a similar advantage as Embodiment 1 above. The movable contaminant detection means 40 can be set up in a location desired by a user, for example, a location where contaminants tend to be generated, or a location where contaminants are to be particularly reduced. Thus, the air purifying operation can be performed with reference to a contamination state of a location where the contaminant detection means 40 is set up. This can preferentially efficiently purify a desired location to improve user's convenience.

In Embodiments 1, 2, the air purifier 1 used in general household has been taken as an example. However, the air purifier of the present invention is not limited to this, but includes various equipments having an air purifying function.

In Embodiment 1, the configuration including the four types of operation modes including the inside cleaning operation, the human avoiding operation, the human area operation, and the indoor air purifying operation has been exemplified. However, the present invention is not limited to this, hut may include at least one operation mode among the four operation modes. The human avoiding operation, the human area operation, and the indoor air purifying operation may be combined with the special air purifying operation for intentionally blowing ozone together with the blown-out air as described above. Thus, the present invention is also applied to an air purifier having no function of performing the inside cleaning operation.

In Embodiment 1, the case is exemplified where at least one of the ozone generation amount and the wind direction of the blown-out air is controlled based on the human detection result and the ozone amount index. However, the present invention is not limited to this, but may have a configuration in which control is performed based on only the human detection result irrespective of the ozone amount index. Also in this case, for example, the human avoiding operation and the indoor air purifying operation may be appropriately used or the human area operation and the indoor air purifying operation may be appropriately used based on the presence or absence of a person. This can achieve both consumer's comfort and efficiency of the air purifying operation with a consideration for an influence of ozone on a person.

In Embodiment 1, ozone is exemplified as a purifying material for purifying air. However, in the present invention, purifying materials such as various radicals or ions not limited to ozone may be controlled. In the present invention, the ozone generation mechanism 15 is exemplified as the purifying material generation means. However, in the present invention, for example, a photocatalyst that receives light to generate a purifying material may be used as the purifying material generation means. In Embodiment 1, the air purifier 1 that can individually blow air from the two outlets 5A, 5B has been exemplified. However, in the air purifier of the present invention, one outlet or three or more outlets may be provided.

Further, the present invention is such that an output of the human detection means 20 may be input to control at least one of parameters including the generation amount of the purifying material, the wind direction, the amount, and the speed of the blown-out air. Specifically, the present invention includes control for changing the amount and the speed of the blown-out air based on the output of the human detection means 20.

DESCRIPTION OF THE REFERENCE NUMERALS

1 air purifier
2 easing
2A panel
2B partition
3 base
3A rotation axis
4 inlet
5A, 5B outlet
6A, 6B blower
7 decontamination unit
8A, 8B air duct
9A, 9B movable louver
10 louver drive
11 rectification mechanism
12 rectification drive
13 horizontal rotation mechanism
14 wind direction adjusting means
15 ozone generation mechanism (purifying material generation means
20 human detection means
21, 40 contaminant detection means
22 operation unit
30 control unit (control means)
41 remote communication means

The invention claimed is:

1. An air purifier comprising:
   a casing having an inlet and an outlet, the outlet being arranged above the inlet;
   a blower for drawing air from the inlet into the casing and blowing the air out of the outlet;
   a decontamination unit configured to remove contaminants from the air drawn into the casing;
   an air duct configured to convey the air from which the contaminants are removed by the decontamination unit to the outlet;
   a wind direction adjuster configured to adjust a wind direction of the air blown out of the outlet, the wind direction adjuster being configured to be able to close the outlet;
   a purifying material generator configured to generate a purifying material in the casing;
   a human detector configured to detect a physical quantity relating to a person, the human detector being provided in the casing; and
   a controller having a function of actuating the wind direction adjuster and the purifying material generator, the controller configured to perform:
      a first operation mode in which the purifying material is generated by the purifying material generator to purify a space in the casing with the wind direction adjuster closing the outlet,
      a second operation mode in which in a case where an air purifying operation is performed with the human detector detecting a person and an index having a correlation to a generation amount of the purifying material being higher than an upper limit reference value, the wind direction of the air blown out of the outlet is set in a direction without the person by the wind direction adjuster,
      a third operation mode in which in a case where an air purifying operation is performed with the human detector detecting a person and the index being equal to or lower than the upper limit reference value, the wind direction of the air blown out of the outlet is set in a direction of the person by the wind direction adjuster, and
      a fourth operation mode in which in a case where an air purifying operation is performed without the human detector detecting a person, the air blown out of the outlet is distributed throughout a room by the wind direction adjuster,
   wherein the controller performs any of the second to fourth operation modes based on a result of the human detector and the index, after the controller performs the first operation mode.

2. The air purifier according to claim 1, further comprising a contaminant detector configured to detect contaminants in the air,
   wherein the controller controls at least one of the generation amount of the purifying material and an output of the blower based on a detection result of the contaminant detector.

3. The air purifier according to claim 2, wherein the contaminant detector comprises a movable contaminant detector being able to be set up away from the casing, the contaminant detector configured to transmit the contaminant detection result to the controller.

4. The air purifier according to claim 1, wherein the controller reduces the generation amount of the purifying material to a human allowable reference value or lower when the human detector detects a person.

5. The air purifier according to claim 1,
   wherein if at least one of a result of the human detector and the index changes while the controller performs any of the second to fourth operation modes, the controller switches the operation mode according to a state after the change.

6. The air purifier according to claim 1, wherein the index having a correlation to the generation amount of the purifying material is a concentration of the purifying material generated by the purifying material generator or an actuation time of the purifying material generator.

7. The air purifier according to claim 1, wherein the purifying material generator has a mechanism for generating at least ozone as the purifying material.

8. The air purifier according to claim 1, wherein the outlet is one of a plurality of outlets and the wind direction adjuster is one of a plurality of the wind direction adjusters, a wind direction of air blown out of each of the plurality of outlets is individually adjusted by each of the plurality of wind direction adjusters.

9. An air purifier comprising:
   a casing having an inlet and an outlet, the outlet being arranged above the inlet;
   a blower for drawing air from the inlet into the casing and blowing the air out of the outlet;
   a decontamination unit configured to remove contaminants from the air drawn into the casing;
   an air duct configured to convey the air from which the contaminants are removed by the decontamination unit to the outlet;
   a wind direction adjuster configured to adjust a wind direction of the air blown out of the outlet, the wind direction adjuster being configured to be able to close the outlet;

a purifying material generator configured to generate a purifying material in the casing;

a human detector configured to detect a physical quantity relating to a person, the human detector being provided in the casing; and a controller having a function of actuating the wind direction adjuster and the purifying material generator, the controller configured to perform:

a first operation mode in which in a case where an air purifying operation is performed with the human detector detecting a person and an index having a correlation to a generation amount of the purifying material being higher than an upper limit reference value, the wind direction of the air blown out of the outlet is set in a direction without the person by the wind direction adjuster, a second operation mode in which in a case where an air purifying operation is performed with the human detector detecting a person and the index being equal to or lower than the upper limit reference value, the wind direction of the air blown out of the outlet is set in a direction of the person by the wind direction adjuster, and a third operation mode in which in a case where an air purifying operation is performed without the human detector detecting a person, the air blown out of the outlet is distributed throughout a room by the wind direction adjuster, wherein if at least one of a result of the human detector or the index changes while the controller performs any of the first to third operation modes, the controller switches the operation mode according to a state after the change.

10. The air purifier according to claim 9, further comprising a contaminant detector configured to detect contaminants in the air, wherein the controller controls at least one of the generation amount of the purifying material and an output of the blower based on a detection result of the contaminant detector.

11. The air purifier according to claim 10, wherein the contaminant detector comprises a movable contaminant detector being able to be set up away from the casing, the contaminant detector configured to transmit the contaminant detection result to the controller.

12. The air purifier according to claim 9, wherein the controller reduces the generation amount of the purifying material to a human allowable reference value or lower when the human detector detects a person.

13. The air purifier according to claim 9, wherein the index having a correlation to the generation amount of the purifying material is a concentration of the purifying material generated by the purifying material generator or an actuation time of the purifying material generator.

14. The air purifier according to claim 9, wherein the purifying material generator has a mechanism for generating at least ozone as the purifying material.

15. The air purifier according to claim 9, wherein the outlet is one of a plurality of outlets and the wind direction adjuster is one of a plurality of the wind direction adjusters, a wind direction of air blown out of each of the plurality of outlets is individually adjusted by each of the plurality of wind direction adjusters.

* * * * *